United States Patent [19]
Chance

[11] Patent Number: 5,899,865
[45] Date of Patent: * May 4, 1999

[54] LOCALIZATION OF ABNORMAL BREAST TISSUE USING TIME-RESOLVED SPECTROSCOPY

[75] Inventor: Britton Chance, Marathon, Fla.

[73] Assignee: Non-Invasive Technology, Inc., Philadelphia, Pa.

[*] Notice: This patent is subject to a terminal disclaimer.

[21] Appl. No.: 08/484,982

[22] Filed: Jun. 7, 1995

Related U.S. Application Data

[60] Division of application No. 08/093,208, Jul. 16, 1993, Pat. No. 5,555,885, which is a continuation-in-part of application No. 08/040,168, Mar. 30, 1993, Pat. No. 5,386,827, and a continuation-in-part of application No. 07/876,364, Apr. 30, 1992, abandoned, which is a continuation of application No. 07/287,847, Dec. 21, 1988, Pat. No. 5,119,815.

[51] Int. Cl.⁶ .................................................. A61B 6/00
[52] U.S. Cl. .................. 600/473; 600/411; 600/427; 600/431; 600/476
[58] Field of Search ...................... 128/664, 665, 128/633, 634, 653.1; 356/317, 318; 250/339.01, 339.02, 339.12, 341.1, 341.2, 341.8; 378/37; 600/310, 342, 473, 475, 476–478, 407, 410, 411, 427

[56] References Cited

U.S. PATENT DOCUMENTS

| | | | |
|---|---|---|---|
| 4,223,680 | 9/1980 | Jobsis | 128/633 |
| 4,281,645 | 8/1981 | Jobsis | 128/633 |
| 4,321,930 | 3/1982 | Jobsis et al. | 128/633 |
| 4,515,165 | 5/1985 | Carroll | 128/664 |
| 4,556,057 | 12/1985 | Hiruma et al. | 128/303.1 |
| 4,570,638 | 2/1986 | Stoddart et al. | 128/665 |
| 4,675,529 | 6/1987 | Kushida | 250/458.1 |
| 4,768,516 | 9/1988 | Stoddart et al. | 128/665 |
| 4,817,623 | 4/1989 | Stoddart et al. | 128/665 |
| 4,832,035 | 5/1989 | Cho et al. | 128/633 |
| 4,895,156 | 1/1990 | Schulze | 128/634 |
| 4,972,331 | 11/1990 | Chance | 364/550 |
| 5,062,431 | 11/1991 | Potter | 128/665 |
| 5,090,415 | 2/1992 | Yamashita et al. | 128/665 |
| 5,119,815 | 6/1992 | Chance | 128/633 |
| 5,139,025 | 8/1992 | Lewis et al. | 128/665 |
| 5,140,989 | 8/1992 | Lewis et al. | 128/665 |
| 5,187,672 | 2/1993 | Chance et al. | 364/550 |
| 5,348,018 | 9/1994 | Alfano et al. | 128/665 |
| 5,349,961 | 9/1994 | Stoddart et al. | 128/665 |
| 5,555,885 | 9/1996 | Chance | 128/665 |

*Primary Examiner*—Ruth S. Smith
*Attorney, Agent, or Firm*—Fish & Richardson P.C.

[57] ABSTRACT

A method of breast tissue examination using time-resolved spectroscopy includes the following steps. A support that includes an input port and an output port separated by a selected distance is positioned relative to the examined breast. Locations of the input and output ports are selected to examine a tissue region of the breast. Light pulses of a selected wavelength and duration less than a nanosecond are introduced into the breast tissue at the input port and detected over time at the detection port. Signals corresponding to photons of detected modified pulses are accumulated over time. Values of a scattering coefficient or an absorption coefficient of the examined breast tissue are calculated based on the shape of the modified pulses. The examined breast tissue is characterized based on the values of the scattering coefficient or the absorption coefficient. Absorbing or fluorescing contrast agents may be introduced into the examined tissue. This method may be used in conjunction with x-ray mammography, needle localization procedure or MRI mammography.

21 Claims, 11 Drawing Sheets

LOCALIZATION OF ABNORMAL BREAST TISSUE USING TIME-RESOLVED SPECTROSCOPY

CROSS REFERENCE TO RELATED APPLICATIONS

This application is a divisional application of U.S. Ser. No. 073,208 filed Jul. 16, 1993, now U.S. Pat. No. 5,555,885, which in turn is a continuation-in-part of a U.S. patent application Ser. No. 08/040,168, filed Mar. 30, 1993 entitled "QUANTITATIVE AND QUALITATIVE IN VIVO TISSUE EXAMINATION USING TIME RESOLVED SPECTROSCOPY" now U.S. Pat. No. 5,386,827 and a continuation-in-part of U.S. patent application Ser. No. 07/876,364 filed Apr. 30, 1992, now abandoned, which is a continuation of U.S. Ser. No. 287,847 filed Dec. 21, 1988, now U.S. Pat. No. 5,119,815, all of which are incorporated by reference as if set forth in their entireties herein.

STATEMENT AS TO FEDERALLY SPONSORED RESEARCH

This invention was made in the course of work supported in part by the U.S. Government, which has certain rights in the invention.

BACKGROUND OF THE INVENTION

The invention features a time-resolved spectroscopic method and apparatus for breast tissue examination.

Breast cancer is among the most common and the most feared malignancies in women. It has an unpredictable course, the treatment is frequently physically and emotionally draining and the risk of metastatic spread persists for many years. Due to its high occurrence rate, routine breast cancer screening, which includes physical examination and x-ray mammography, plays an important role in current health care. X-ray mammography can detect over 90% of all masses and increases the 10-year survival rate to about 95% for patients with cancers solely detected by mammography. Although the modern mammography uses a low-dose of x-rays, it still involves some small risk of inducing cancers by the radiation. Other tests, such as magnetic resonance imaging (MRI) and gadolinium enhanced MRI, have been used successfully for detection of breast tumors and may be used routinely for screening in the future.

After a small suspicious mass is detected in the breast non-invasively, an excisional biopsy is usually performed to exclude or diagnose malignancy. The biopsy specimen is removed under local anesthesia and is used for histopathological diagnosis. The statistics show that in about 75% of the excisional biopsies, the biopsied tissue is diagnosed to be benign. Thus, a majority of patients undergoes this unpleasant and costly procedure unnecessarily. Furthermore, it has been suggested that the excisional biopsy may cause spreading of the malignant tumor cells.

Therefore, a non-invasive, relatively inexpensive technique that can detect and characterize breast tumors may find its place in today's health care, alone or in conjunction with the above-mentioned techniques.

SUMMARY OF THE INVENTION

The invention features an system and a method for breast tissue examination using time-resolved spectroscopy In general, in one aspect, the method includes the following steps. A support that includes an input port and an output port separated by a selected distance is positioned relative to the examined breast. Locations of the input and output ports are selected to examine a tissue region of the breast. Light pulses of a selected wavelength and duration less than a nanosecond are introduced into the breast tissue at the input port and detected over time at the detection port. Signals corresponding to photons of detected modified pulses are accumulated over the arrival time of detected photons. Values of a scattering coefficient or an absorption coefficient of the examined breast tissue are calculated based on the shape of the modified pulses. The examined breast tissue is characterized based on the values of the scattering coefficient or the absorption coefficient.

In general, in another aspect, the method includes the following steps. A support that includes an input port and an output port separated by a selected distance is positioned relative to the examined breast. Locations of the input and output ports are selected to examine a tissue region of the breast. Light pulses of a selected wavelength and duration less than a nanosecond are introduced into the breast tissue at the input port and detected over time at the detection port. Signals corresponding to photons of detected modified pulses are integrated over at least two selected time intervals separately spaced over the arrival time of the modified pulses. A value of an absorption coefficient of the examined breast tissue is calculated based on the shape of the modified pulses. The examined breast tissue is characterized based on the value of the absorption coefficient.

In this aspect, the method may include further steps. The detected photons are integrated over other selected time intervals separately spaced over the arrival time of the modified pulses. Time dependence of the light intensity is determined based on the number of photons integrated over each time interval, and a value of a scattering coefficient of the examined breast tissue is determined. The examined breast tissue is characterized based on the value of the scattering coefficient.

Preferred methods use the above-described steps and additional steps as follows.

The input port and the output port are moved to a different location to examine another tissue region of the breast. Values of the scattering coefficient or absorption coefficient are again determined by repeating the above-described steps for the newly selected tissue region. The tissue region is characterized using the additional values of the scattering coefficient or the absorption coefficient.

The above-described steps are performed over several tissue regions to examine the entire breast.

The characterizing step includes comparing the calculated values of the scattering or absorption coefficient with selected values of scattering or absorption coefficient, respectively.

The selected values of the scattering and absorption coefficient correspond to normal breast tissue, normal contralateral breast tissue or series of homogenous breast tumors.

The characterizing step includes comparing the calculated values of the scattering coefficient or the absorption coefficient with selected values of the scattering coefficient or the absorption coefficient, respectively.

If the above-recited characterizing step reveals that the examined tissue includes abnormal tissue, the following steps are performed. Other locations of the input port and the output port are selected to define a new tissue region proximate to the region having abnormal tissue. The values of the scattering coefficient or the absorption coefficient of the newly selected tissue region are determined by applying the corresponding above-recited steps. Abnormal breast tissue is localized by comparing values of the scattering coefficient or the absorption coefficient of different selected tissue regions. The type of the abnormal tissue may be determined by comparing values of the scattering coefficient or the absorption coefficient of the localized tissue to values of the scattering coefficient or the absorption coefficient corresponding to selected tissue masses.

The tissue masses include one of the following: carcinoma, fibroadenoma or fibrocystic tissue.

The size and location of the abnormal tissue region is determined.

If the above-recited characterizing step reveals that the examined tissue, includes abnormal tissue further the following steps are performed. A contrast agent exhibiting known optical properties at the selected wavelength is injected into the blood stream of the subject. Other locations of the input port and the output port are selected to define a new tissue region proximate to the region having abnormal tissue. The values of the scattering coefficient or the absorption coefficient of the newly selected tissue region are determined. The abnormal breast tissue is localized by comparing values of the scattering coefficient or the absorption coefficient of different selected tissue regions. The type of the abnormal tissue may be determined by comparing values of the scattering coefficient or the absorption coefficient of the localized tissue to values of the scattering coefficient or the absorption coefficient corresponding to selected tissue masses comprising the contrast agent.

If the above-recited characterizing step reveals that the examined tissue includes abnormal tissue, further the following steps are performed. A contrast agent exhibiting known optical properties at the selected wavelength is injected into the abnormal tissue. Other locations of the input port and the output port is selected. The values of the scattering coefficient or the absorption coefficient of the newly selected tissue region are determined. The abnormal breast tissue is localized by comparing values of the scattering coefficient or the absorption coefficient of different selected tissue regions.

The type of the abnormal tissue may be determined by comparing values of the scattering coefficient or the absorption coefficient of the localized tissue to values of the scattering coefficient or the absorption coefficient corresponding to selected tissue masses comprising the contrast agent.

The contrast agent is a fluorescing material or absorbing material. The contrast agent is preferentially absorbed by the tissue mass.

The above described steps are performed in conjunction with x-ray mammography, MRI mammography or a needle localization procedure.

In another aspect, the invention features a system for performing the above-described method.

DESCRIPTION OF THE PREFERRED EMBODIMENTS

Figure 1:
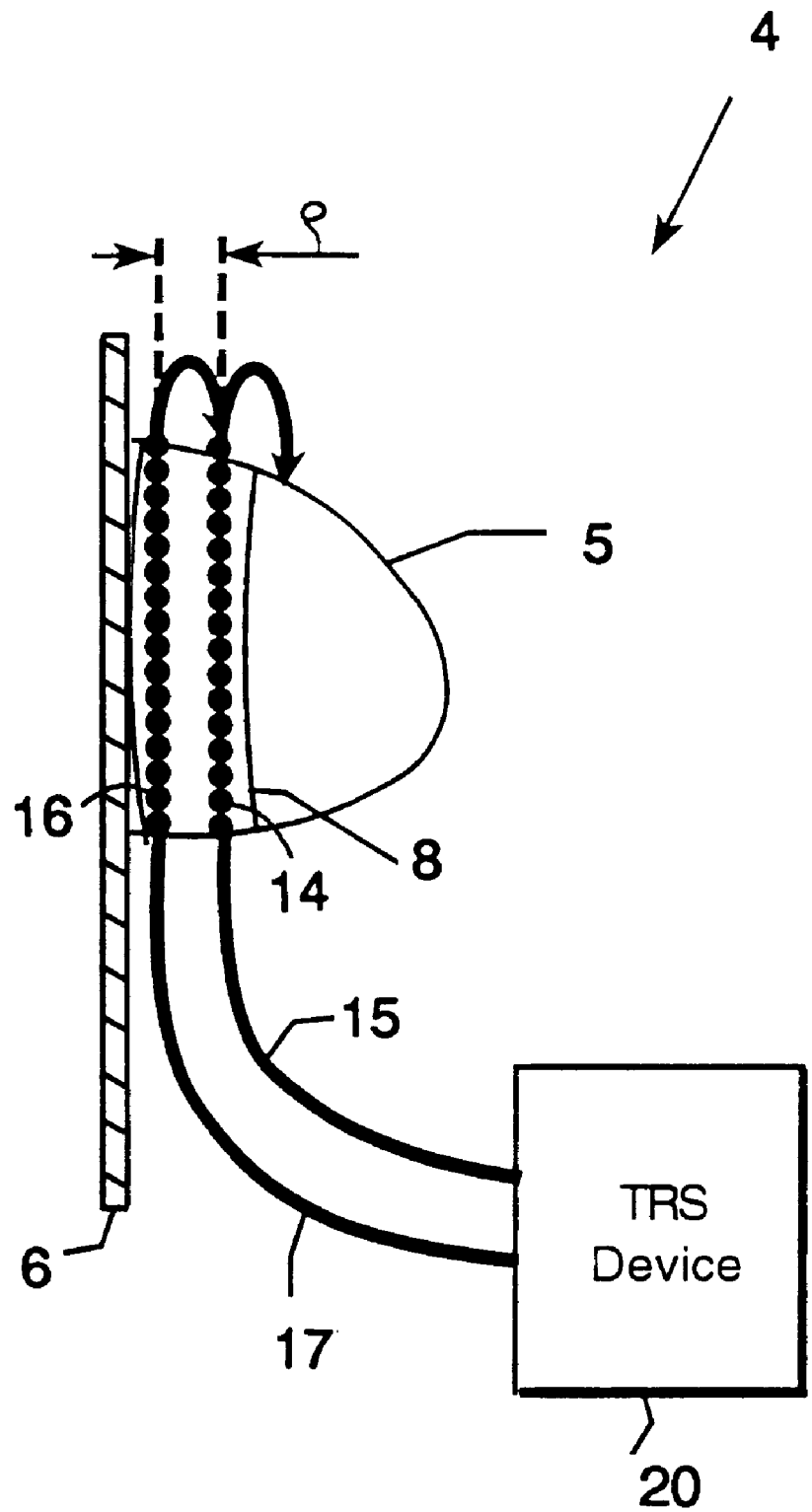
FIG. 1 depicts diagrammatically a time-resolved spectroscopic system for breast tissue examination.

FIG. 1 depicts a breast tissue examination system 4 placed on a human breast 5 for breast tissue examination. The system includes an optical fiber support 8 with multiple input ports 14 and multiple output ports 16. Support 8 is placed around breast 5 so that input ports 14 and output ports 16 define irradiation locations and detection locations on the skin of breast 5, respectively. Connected to selected input and output ports are optical fibers 15 and 17, respectively. System 4 uses a TRS device 20 that is either a single photon tissue resolved apparatus 20A or a time resolved apparatus 20B using boxcar type integration shown in FIGS. 2 and 3, respectively.

Figure 1A:
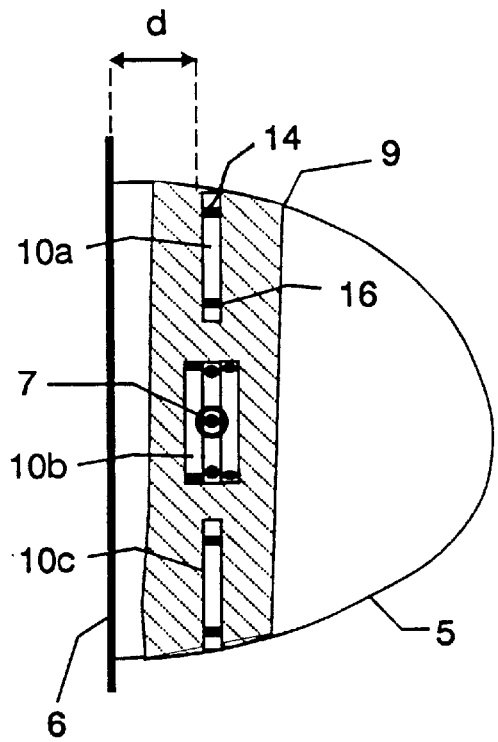
FIGS. 1A, 1B, 1C and 1D depict different embodiments of an optical fiber support for breast tissue examination.
Figure 1B:
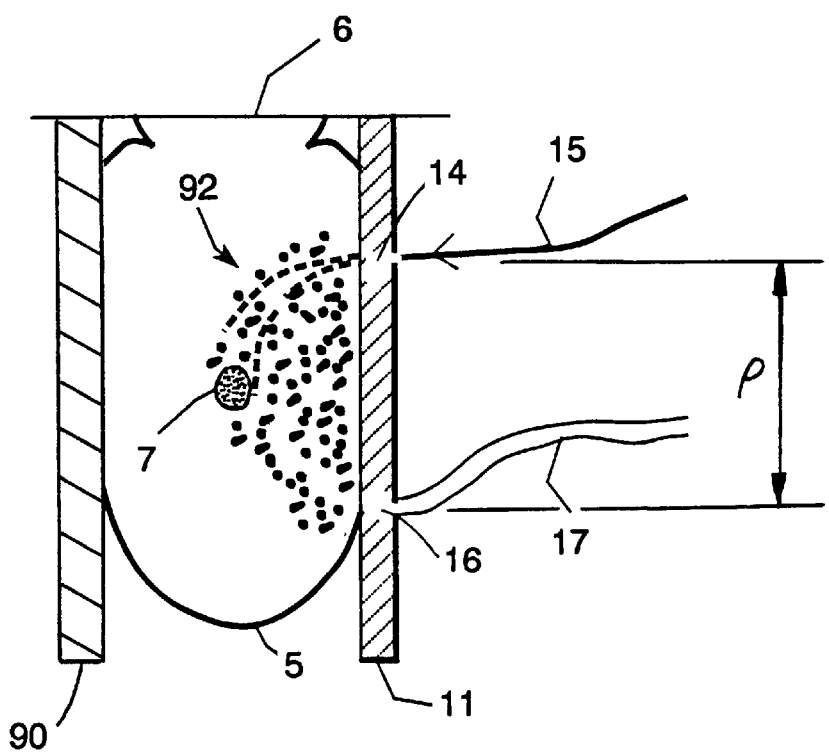
Figure 1C:
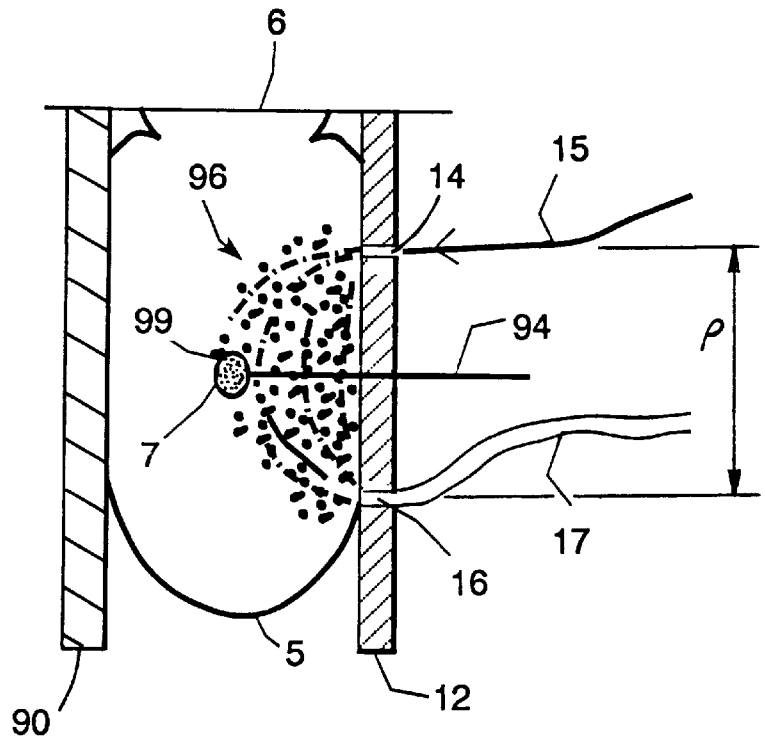
Figure 1D:
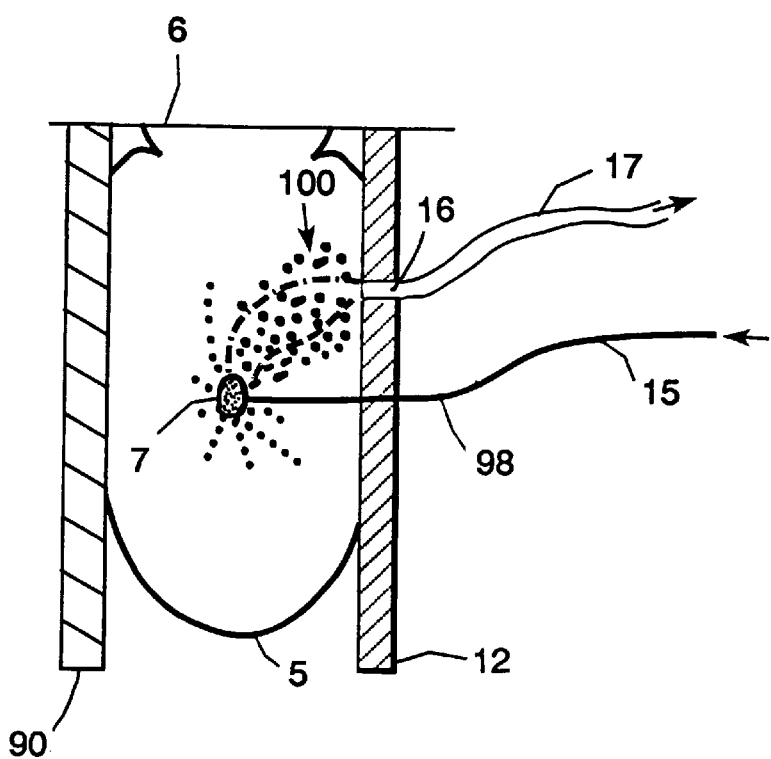

Referring also to FIGS. 1A, 1B, 1C and 1D, system 4 uses different types of the optical fiber supports designed to introduce and detect photons at selected locations and thus shape the optical field. The optical fiber supports are made of flexible or rigid materials and are shaped to accommodate breasts of different volumes. Furthermore, the inside surface of the supports may include material of known scattering and absorptive properties. The material is selected to either return back to the breast tissue photons escaping through the skin (i.e., a low absorber and high scatterer) or provide additional paths for the escaping photons to the detector (i.e., the material has substantially the same optical properties as normal breast tissue). The supports are designed for use with a time-resolved spectrophotometer (TRS) alone or in conjunction with x-ray mammography, MRI or a needle localization procedure. Specifically, fiberoptic support 9 shown in FIG. 1A includes three sets of the input and detection ports labeled 10a, 10b, and 10c. Sets 10a and 10c are used to measure control data and set 10b is used to examine a suspected mass 7. Furthermore, support 9 enables precise characterization of the distances between the three sets, between input ports 14 and detection ports 16 ($\rho$) and from the chest wall 6 to each set ($d_n$). Supports 11 and 12, shown in FIGS. 1B, 1C and 1D, are used with x-ray mammography and needle localization procedure, respectively, and their functions are described below.

Figure 2:
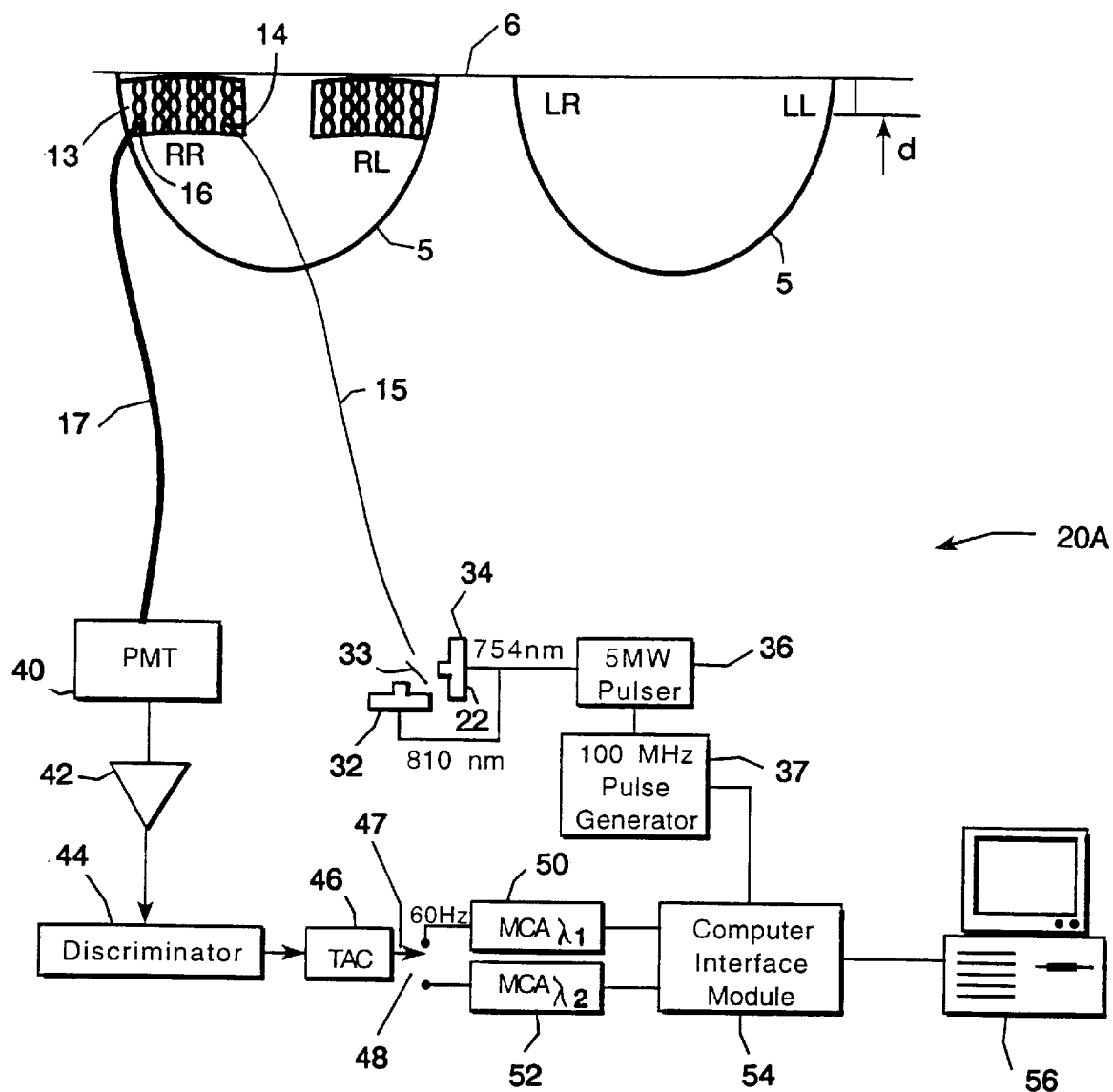
FIG. 2 depicts diagrammatically a single photon counting TRS apparatus arranged for breast tissue examination.

Referring to FIG. 2, a dual wavelength, time correlated-single photon counting TRS apparatus 20A is connected to support 13 positioned on breast 5. Pulsed laser diodes 32 and 34 (model PLP-10 made by Hamamatsu, Japan), are driven by a 5 mW pulser 36 connected to a 100 MHz pulse generator 37, and generate light pulses on the order of 500 psec or less. The light from laser diodes 32 and 34 is electro-mechanically time shared using a 60 Hz vibrating mirror 33 and is coupled to one end of optical fiber 15. Optical fiber 15, which has about 200 $\mu$m diameter, alternatively conducts pulses of 754 nm and 810 nm light to input port 14. The introduced photons migrate in the examined breast tissue and some of them arrive at output port 16. Optical fiber 17 collects photons of the modified pulses from an area of about 10 mm² and transmits them to a PMT detector 40.

Figure 3:
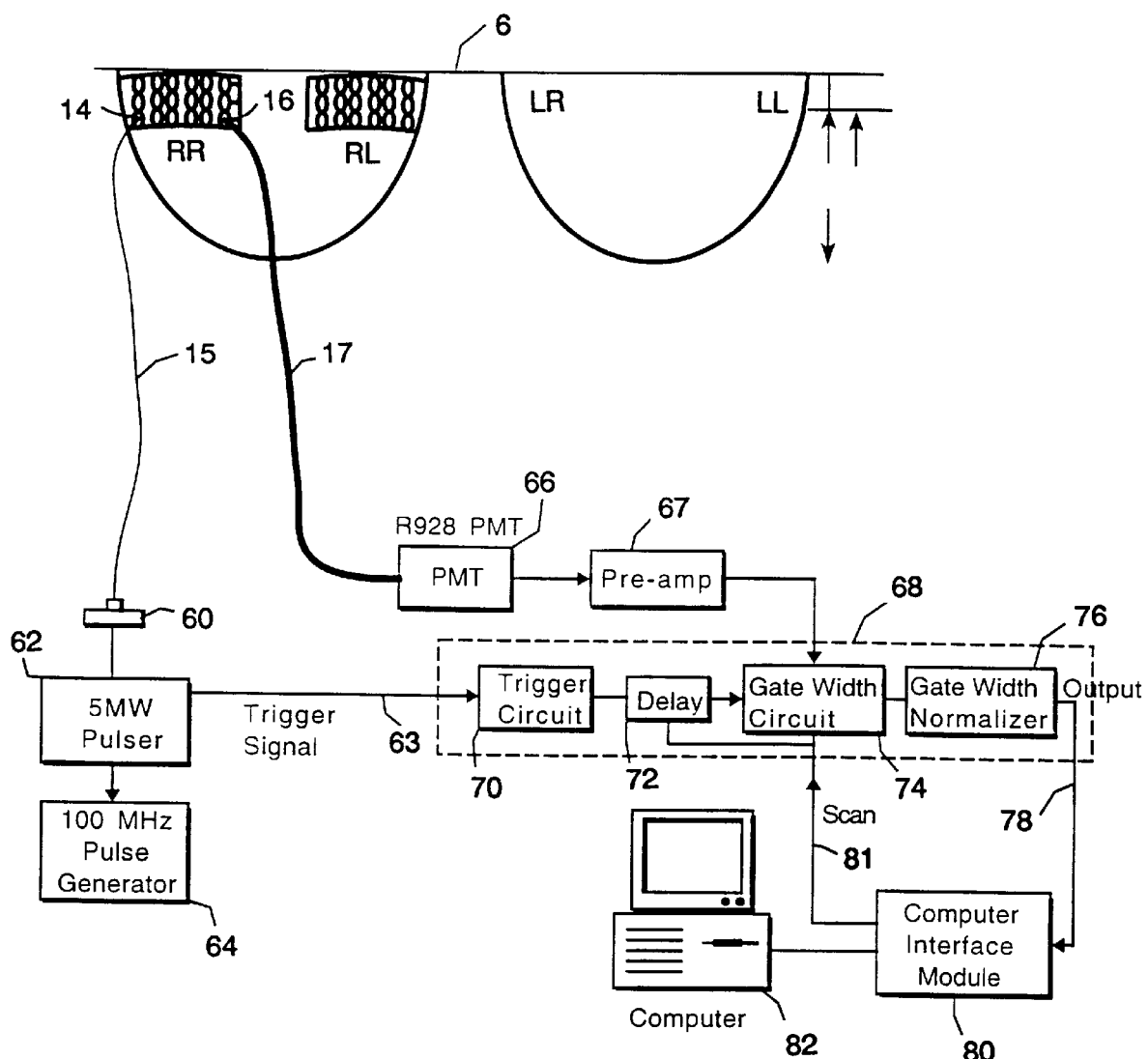
FIG. 3 depicts diagrammatically a TRS boxcar apparatus arranged for breast tissue examination.

The output of PMT 40 is connected to a wide band amplifier 42 with appropriate roll-off to give good pulse shape and optimal signal to noise ratio. Output signals from amplifier 42 are sent to a high/low level discriminator 44, which is a pulse amplitude discriminator with the threshold for pulse acceptance set to a constant fraction of the peak amplitude of the pulse. Next, the discriminator pulses are sent to a time-to-amplitude convertor (TAC) 46. TAC 46 produces an output pulse with an amplitude proportional to the time difference between the start and stop pulses received from pulser 36. The TAC pulses (47) are routed by a switch 48 to either a multichannel analyzer (MCA) 50 or an MCA 52. Switch 48 operates at 60 Hz and is synchronized with mirror 33. The photon emission, detection cycle is repeated at a frequency on the order of 10 MHz. Each MCA collects only a single photon for each light pulse introduced to the tissue. Each MCA acquires and sums photons of only one designated wavelength and stores the corresponding pulse of a shape that depends on properties of the examined tissue. The pulses are preferably accumulated over about 2 to 3 minutes so that at least $10^5$ counts are collected at the maximum of the pulse shape. The detected pulse shape is analyzed by a computer 56. Computer 56 is connected to pulse generator 37 and MCAs 50 and 52 via an interface module 54 and is adapted to control the entire operation of the system Alternatively, TRS apparatus 20 represents a boxcar TRS apparatus 20B, as shown in FIG. 3. A pulsed laser diode 60 is driven by a 5 mW pulser 62 connected to a 100 MHz pulse generator 64. Laser diode 60 generates a train of 100 ps light pulses of 754 nm wavelength coupled to optical input fiber 15. The light pulses are introduced to breast tissue at input port 14. The introduced photons migrate in the examined tissue and a portion of them arrives at an output port 16. In the migration process, the input pulse has been modified by the scattering and absorptive properties of the examined tissue. Photons arriving at detection port 16 are transmitted by optical fiber 17 to a detector 66, (for example, Hamamatsu photomultipliers R928, R1517, MCP R1712, R1892).

Figure 3A:
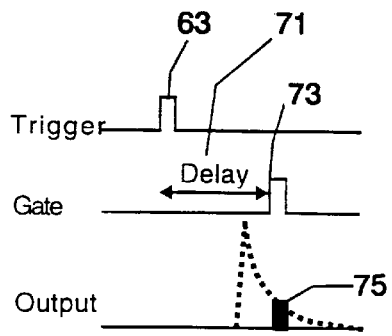
FIG. 3A shows a timing diagram of the apparatus of FIG. 3.

The output of detector 66 is amplified in a wide band preamplifier/impedance changer 67 and coupled to a boxcar integrator 68. Integrator 68 activated by a pulse gate 73 collects all arriving photons over a predetermined time interval 75, as shown in FIG. 3A. The integrator output (78) is sent to computer interface module 80 and computer 82. Computer 82 stores the total number of counts detected during the collection interval of integrator 68.

Integrator 68 includes a trigger 70, which is triggered by a signal 63 from pulser 62. Trigger 70 activates a delay gate 72 which, in turn, starts counting of all detected photons during the time interval specified by a gate width circuit 74. Output from a gate width normalizer 76 is an analog signal or a digital signal representing all photons that arrived at detection port 16 during the preselected gate width interval (75). A suitable integrator is a boxcar SR 250 manufactured by Stanford Research Systems.

Depending on the application, computer 82 sets the delay time (71) of delay gate 72 and the gate width time (75) of gate width circuit 74. Gate width normalizer 76 adjusts the width of the integration time depending on the detected signal level. The gate width may be increased logarithmically for signals at $t \gg t_{max}$, wherein the detected number of photons decreases exponentially; this increases the signal-to-noise ratio. Furthermore, computer 82 can scan the integration gate widths over the whole time profile of the detected pulse. By scanning the delay times (71) and appropriately adjusting the gate widths (75), the computer collects data corresponding to the entire detected pulse. Subsequently, computer 82 calculates the shape (85) of the detected pulse and stores the time dependent light intensity profile I(t).

Figure 3B:
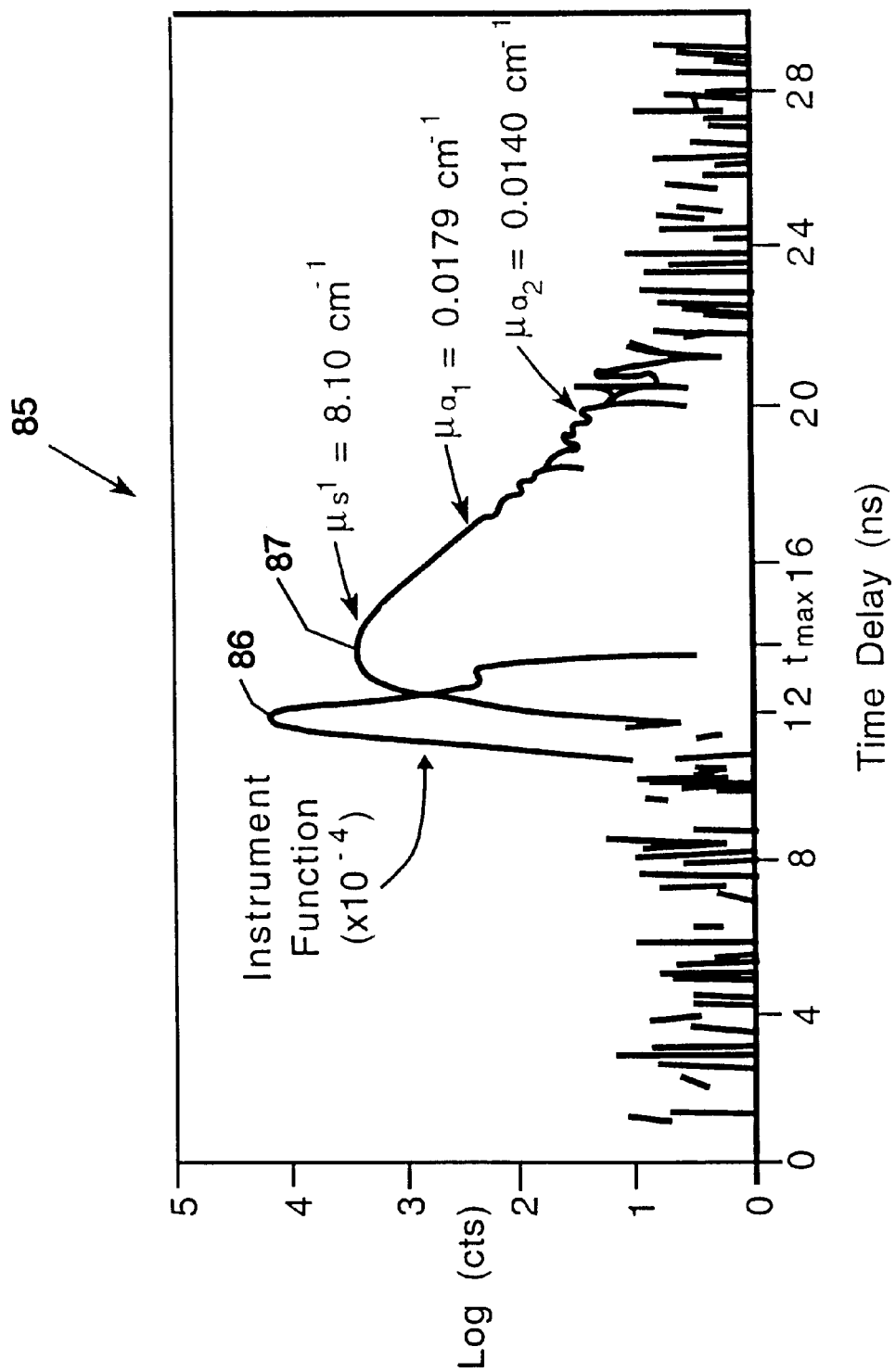
FIG. 3B shows a typical time resolved spectrum collected by the apparatus of FIG. 3.

The pulse shape, I(t), detected either by apparatus 20A or apparatus 20B possesses information about the scattering and absorptive properties of the examined breast tissue and is used to determine the scattering and absorption coefficients. Referring to FIG. 3B, a test measurement was performed on apparatus 20A and found that due to a somewhat slow response time, the detector broadens the reflectance profile, as seen on spectrum 86. Thus the experimental spectra (87) are deconvoluted to separate the instrumental response from the profile dispersion due to the diffusion. The deconvolution yields about 6% increase in the value of $\mu_a$ and about 23% decrease in the value of $\mu_s$.

The examined tissue region is defined by the distribution of photon pathlengths forming an optical field in the tissue. The size and shape of the optical field is a function of the input-output port separation ($\rho$) as well as the optical properties of the tissue (i.e., absorption coefficient, $\mu_a$, scattering coefficient, $\mu_s$, and the mean cosine of anisotropic scattering, g). The general diffusion equation is used to describe the photon migration in tissue, as analyzed by E. M. Sevick, B. Chance, J. Leigh, S. Nioka, and M. Maris in Analytical Biochemistry 195, 330 (1991), which is incorporated by reference as if fully set forth herein. The diffusion equation is solved for the intensity of detected light in the reflectance geometry, R($\rho$,t), or the transmittance geometry T($\rho$,d,t). In the reflectance geometry, in a semi-infinite media with the separation of the input and output ports on the order of centimeters, the absorption coefficient is a function of the reflectance spectrum as follows:

$$\frac{d}{dt}\log_e R(\rho, t) = \frac{-5}{2t} - \mu_a c + \frac{\rho^2}{4Dct} \quad (1)$$

For $t \to \infty$ the absorption coefficient $\mu_a$ is determined as follows:

$$\lim_{t \to \infty} \frac{d}{dt}\log_e R(\rho, t) = -\mu_a c \quad (2)$$

wherein $\rho$ is the separation between input and detection ports and c is speed of light in the medium However, it is difficult to measure the at $t \gg t_{max}$ because in this region the data show substantial noise. Thus, to measure $\mu_a$ at $t \gg t_{max}$, requires determination of the pulse shape at a high number of counts.

If the approximation of infinite time is not valid, Eq. 1 can be rewritten to obtain $\mu_a$ as follows:

$$\mu_a c = -\frac{d}{dt}\log_e R(\rho, t) + \frac{\rho^2}{4Dct} - \frac{5}{2t} \quad (3)$$

The value for D can either be the average value obtained from numerical simulations or a value specific to the type of tissue being measured.

The effective scattering coefficient $(1-g) \cdot \mu_s$ is determined as follows:

$$(1-g)\mu_s = \frac{1}{\rho^2}(4\mu_a c^2 t_{max}^2 + 10ct_{max}) - \mu_a \quad (4)$$

wherein $t_{max}$ is the delay time at which the detected reflectance time profile $(R(\rho,t)=I(t))$ reaches maximum. After detecting the pulse shape corresponding to the examined tissue the computer calculates the absorption coefficient $(\mu_a)$, and the scattering coefficient $(\mu_s)$. The absorption coefficient is quantified by evaluating the decaying slope of the detected pulse, using Eqs. 2 or 3. The effective scattering coefficient, $(1-g)\cdot\mu_s$, is determined from Eq. 4.

The breast screening procedure starts by selecting a support with appropriate arrangements of input ports 14 and output ports 16. The absorptive and scattering properties of the tissue are measured for one set of ports and then the optical field is transferred by using another set of ports. The entire breast is examined by selecting sequentially different ports. In the reflection geometry, the optical field can be represented by a three dimensional, "banana-shaped" distribution pattern or, in the transmission geometry, a "cigar-shaped" distribution pattern. In the "banana-shaped" pattern, the shallow boundary is due to the escape of photons that reach the air-scatterer interface while the deeper boundary is due to attenuation of long path photons by the absorbers. The penetration depth of the photons is about one half of the port separation ($\rho$). During the screening procedure, the computer calculates $\mu_a$ and $\mu_s$ for the entire breast and compares the measured values with threshold values of $\mu_a$ and $\mu_s$ of normal tissue or series of $\mu_a$ and $\mu_s$ values of different homogeneous tumor types. As is shown in FIGS. 5A through 5F, from one person to another there is some variation in $\mu_a$ and $\mu_s$ for normal tissue, but only a very small variation between the left breast and the right breast of the same person. Cancerous tissue, which is usually highly perfused, exhibits higher values of $\mu_a$ and $\mu_s$ than fibrous tissue. Normal tissue, which has a relatively high amount of fat, exhibits the lowest values of $\mu_a$ and $\mu_s$.

Alternatively, instead of calculating $\mu_a$ and $\mu_s$, the system can calculate an average pathlength of the migrating photons. From the detected and deconvoluted photon intensity profile, R(t), a mean pathlength of the distribution of pathlengths <L> is determined as follows:

$$\langle L \rangle = \frac{c}{n}\int_0^\infty \frac{I(t)t\partial t}{\int_0^\infty I(t)\partial t} \quad (5)$$

wherein c is the speed of light in vacuum and n≈1.36 is the average refractive index of tissue.

If a breast tumor is outside of the optical field, it does not alter the banana-shaped distribution of pathlengths. As the optical field is moved closer to the breast tumor, which is a strongly absorbing mass, the photons that have migrated the farthest distance from the input and detection ports are eliminated by the absorption process. Since photons with the longest pathlengths are absorbed by the mass, the system detects reduction in the average pathlength. When the optical field is moved even closer to the mass, some of the detected photons now migrate around the mass without being absorbed; this is detected as lengthening of the distribution of pathlengths. Thus, the average pathlength measurement can reveal location of the breast mass.

In the screening process, the breast tissue is characterized by several tissue variables which may be used alone or in combination. TRS device 20 measures the absorption coefficient, the scattering coefficient, the blood volume or tissue oxygenation using one or more selected wavelengths of the laser. The wavelengths are sensitive to naturally occurring pigments or contrast agents that may be preferentially absorbed by the diseased tissue. Suitable naturally occurring pigments are, for example, hemoglobin (Hb) or oxyhemoglobin (HbO$_2$) sensitive to 754 nm and 816 nm, respectively.

Alternatively, suitable color dyes, such as cardio-green or indocyinin-green, may be injected to the blood system alone or bound to a vehicle such as a gadolinium contrast agent, which is preferentially absorbed by tumors in the first five to ten minutes. An appropriate wavelength is selected for the color dye, for example, cardio-green exhibits maximum absorption at 805 nm.

The computer can create "maps" of the breast by mapping the spacial variation of the measured values for $\mu_a$, $\mu_s$, blood volume or hemoglobin saturation. The resolution is enhanced when several tissue variables are mapped. The blood volume is measured using a pair of contrabestic wavelengths (e.g., 754 nm and 816 nm) or the isobestic wavelength (i.e., 805 nm). The hemoglobin saturation (Y) is measured at two wavelengths (e.g., 754 nm and 816 nm) and is calculated by taking the ratio of absorption coefficients at these wavelengths and then using the following equation:

$$Y(\times 100\%) = \frac{38 - 18\frac{\mu_a^{754}}{\mu_a^{816}}}{25 + 3\frac{\mu_a^{754}}{\mu_a^{816}}} \quad (6)$$

wherein the coefficients are determined from the extinction values of hemoglobin at 754 nm and 816 nm that are $\epsilon_{Hb}$=0.38 cm$^{-1}$ mM$^{-1}$, $\epsilon_{Hb}$=0.18 cm$^{-1}$mM$^{-1}$, respectively, and the difference in extinction coefficients between oxyhemoglobin and hemoglobin that are $\Delta\epsilon_{HbO-Hb}$=0.025 cm$^{-1}$ mM$_{-1}$ and $\Delta\epsilon_{HbO-Hb}$=0.03 cm$^{-1}$ mM$^{-1}$, respectively.

In another preferred embodiment, TRS apparatus 20 is used in combination with x-ray mammography. The combined procedure is performed if a suspected mass is detected by the above-described optical method, x-ray mammography or another screening method.

Referring to FIG. 1B, breast 5 is compressed in either a horizontal or vertical position between an x-ray film case 90 with the x-ray film and a support 11 with input ports and output ports located on a grid. An x-ray mammogram is taken to determine location of suspected mass 7 relative to the grid. Suitable input port 14 and output port 16 are selected so that the introduced optical field 92 encompasses mass 7. Then, TRS apparatus 20A or 20B is used to measure $\mu_a$, $\mu_s$, the blood volume or oxygen concentration of the examined tissue using the above-described techniques. The measured values are again compared to the values corresponding to normal tissue or different types of diseased tissue to characterize the mass. If an unequivocal result is obtained, an exploratory excisional biopsy is not needed.

In another preferred embodiment, TRS apparatus 20 is used in combination with the needle localization procedure. The needle localization procedure locates the mass that is then examined by system 4. Furthermore, a needle used in the needle localization procedure may introduce an optical fiber directly to mass 7.

Referring to FIGS. 1C and 1D, breast 5 is compressed between x-ray film case 90 and a support 12 with input ports and output ports located on a grid and a centrally located opening for a needle 94 or a needle 98. One or more x-ray mammograms are taken to determine the location of suspected mass 7 relative to the grid and to the needle opening. The needle is inserted into the breast and the needle tip is positioned in the center of mass 7. Additional x-ray mammograms may be taken to verify or adjust the position of the needle.

As shown in FIG. 1C, if the needle is used only to localize mass 7, input port 14 and output port 16 are selected so that their separation is equal or larger than two times the depth of mass 7. This separation assures that the introduced optical field 96 encompasses mass 7. After needle 94 is positioned, a tiny wire is inserted into the mass and left there for marking purposes. TRS apparatus 20 measures $\mu_a$, $\mu_s$, blood volume or oxygen concentration of the examined tissue using the above-described techniques. The measured values are again compared to the values of normal tissue and different types of diseased tissue to characterize tissue of mass 7.

As shown in FIG. 1D, needle 98 positions an end 99 of optical input fiber 15 directly inside mass 7. Here, the optical fiber with a diameter of about 100 $\mu$m or less is threaded inside needle 98 and end 99 is slightly extended from the needle so that the introduced photons are directly coupled to mass 7. The location of detection port 16 defines optical field 100. In this arrangement, all detected photons migrate in the targeted tissue; this increases the relative amount of the targeted tissue being examined and thus increases the resolution of the system. To compare tissue of mass 7 with normal tissue, the same geometry of the input port and the detection port is used to measure the optical properties of the contralateral breast. Alternatively, in the same breast, needle 98 is moved outside of mass 7 so that the positions of the optical fiber end 99 and detection port 16 define an optical field completely removed from mass 7. To characterize the mass, the values of $\mu_a$ and $\mu_s$ measured for mass 7 are compared either to the values of normal tissue measured in the same arrangement or to values of different types of diseased tissue.

In another embodiment, the detection contrast is enhanced using fluorescing contrast agents. A tumor is permeated with a fluorescing contrast agent that has a decay time of less than 1 nsec, and the labeled tumor is then again examined using TRS device 20. Suitable agents emit fluorescing radiation in the range of 800 nm to 1000 nm, for example, carbocyanene dyes or porphorin compounds.

Figure 4:
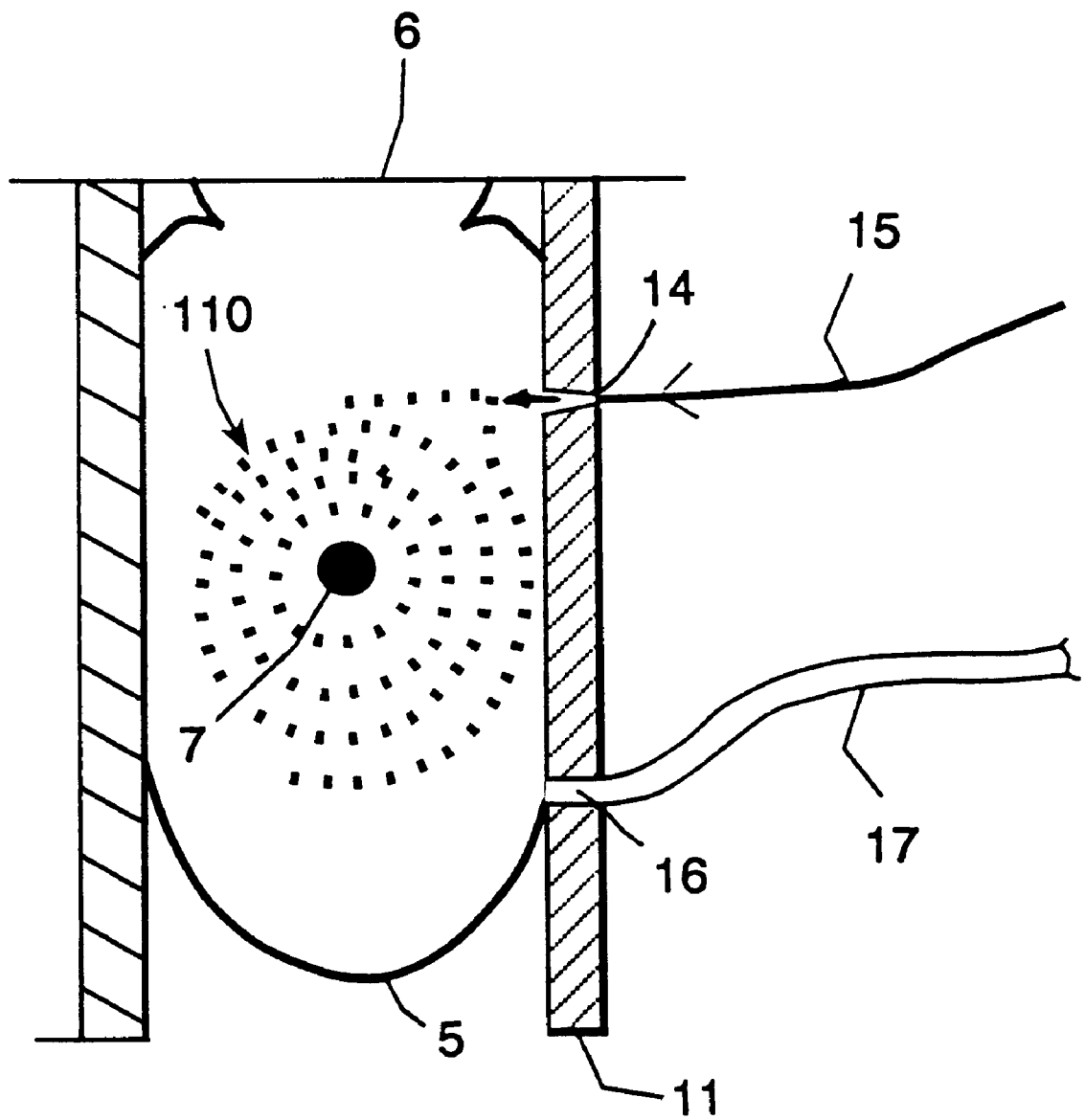
FIG. 4 depicts diagrammatically examination of breast tissue using a fluorescing contrast agent.

Referring to FIG. 4, the fluorescing contrast agent is injected to the blood system alone or bound to a vehicle, such as a gadolinium contrast agent, which is initially preferentially absorbed by a breast tumor. Alternatively, the fluorescing agent is injected directly into the tumor. TRS device 20 generates 150 psec light pulses introduced into breast 5 at input port 14. The introduced photons of selected excitation wavelength reach tumor 7 and excite a fluorescing radiation 110, which propagates in all directions from tumor 7. The photons of fluorescing radiation 110 migrate in the examined breast tissue and some of them arrive at output port 16. Output port 16 has an interference filter that passes only photons at the wavelength of fluorescing radiation 110. Optical fiber 17 collects the transmitted photons, which are delivered to the PMT detector. System 4 may detect fluorescing radiation 110 at several output ports at the same time or move the ports to different positions on the fiber optic support.

TRS device 20 detects the pulses of fluorescing radiation 110; the shape of these pulses depends on the decay time of the fluorescing agent and optical properties of both the tumor tissue and the normal breast tissue.

Figure 4B:
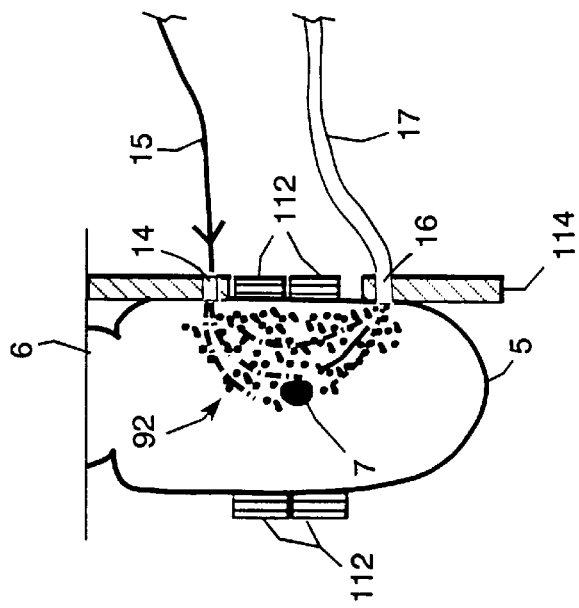
FIGS. 4A and 4B depict diagrammatically examination of breast tissue using MRI and time-resolved spectroscopy.
Figure 4A:
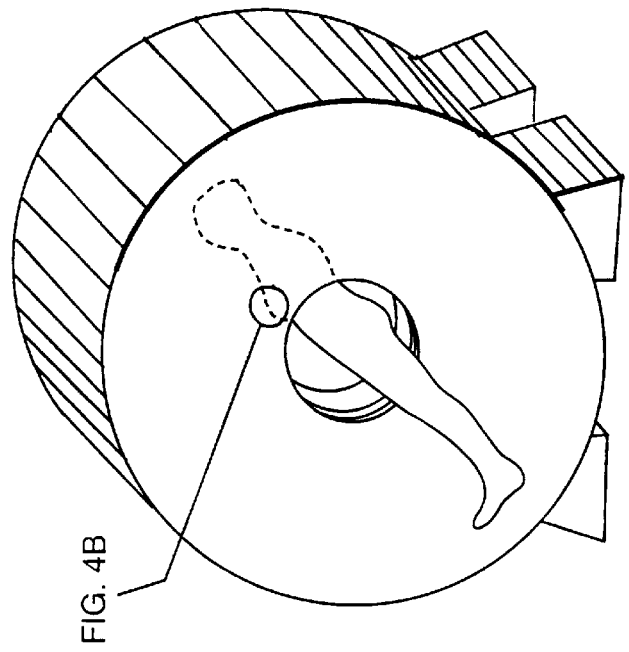

In another embodiment, referring to FIGS. 4A and 4B, TRS apparatus 20 is used in combination with MRI. MRI examines the breast with or without using a rare earth contrast agent. A network of surface coils 112 is cooperatively arranged with a fiberoptic support 114, which is constructed for use with MRI. The network of coils 112 and support 114 are appropriately located around the examined breast. At the same time as the MRI data are collected, TRS apparatus 20 collects the optical data. If an abnormal mass is detected, MRI identifies the size and location of the mass. The optical data are then used to characterize the mass. Optical contrast agents may be used alone or in combination with the rare earth contrast agents, as described above.

EXPERIMENTS

Preliminary experiments were conducted under a pre-approved protocol and after receiving informed consent of women with normal breast tissue and of women having a mass detected in their breast.

Figure 5A:
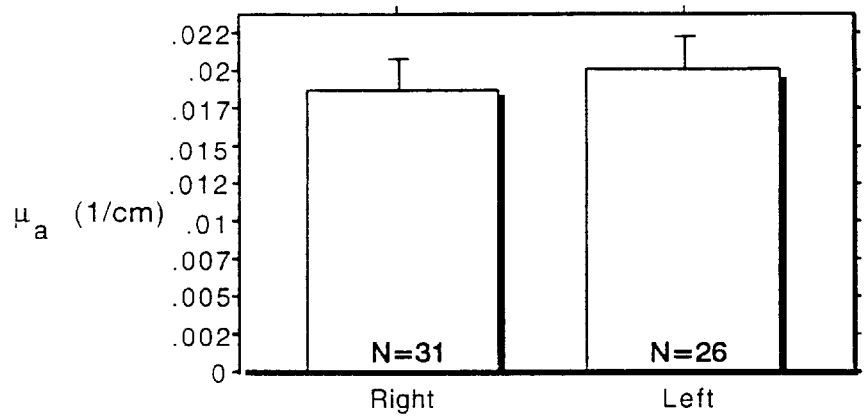
FIGS. 5A, 5B, 5C, 5D, 5E and 5F display values of the absorption coefficient and the scattering coefficient of normal breast tissue measured at different locations of the right breast and of the left breast.
Figure 5C:
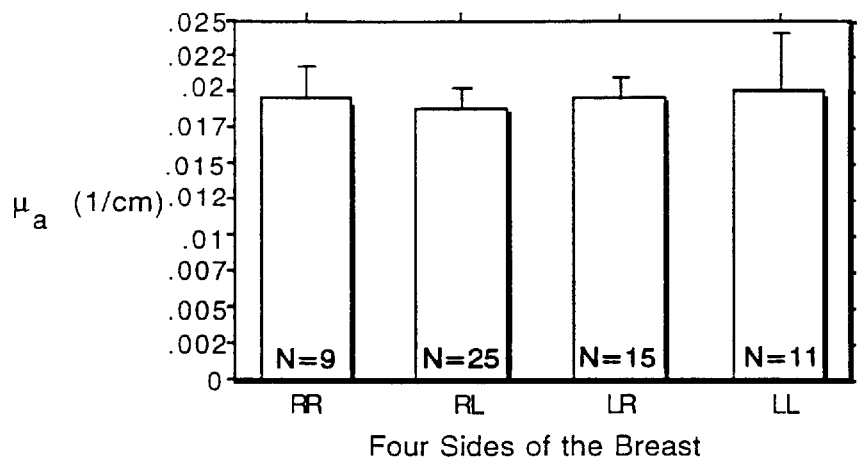
Figure 5E:
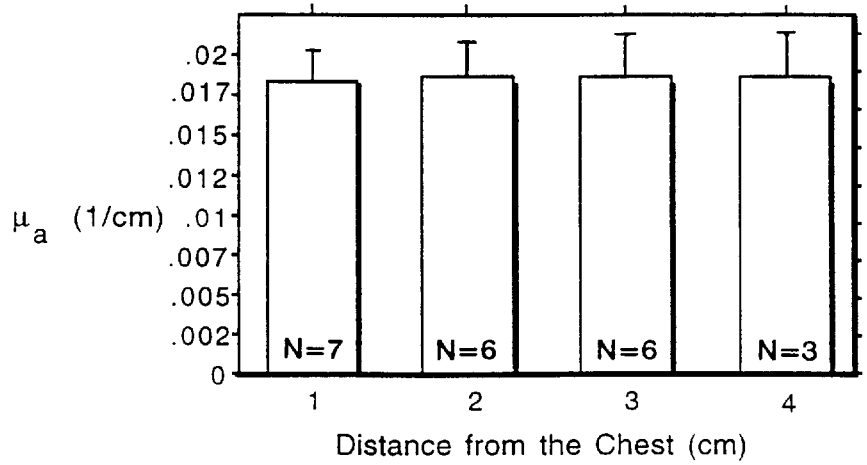
Figure 5B:
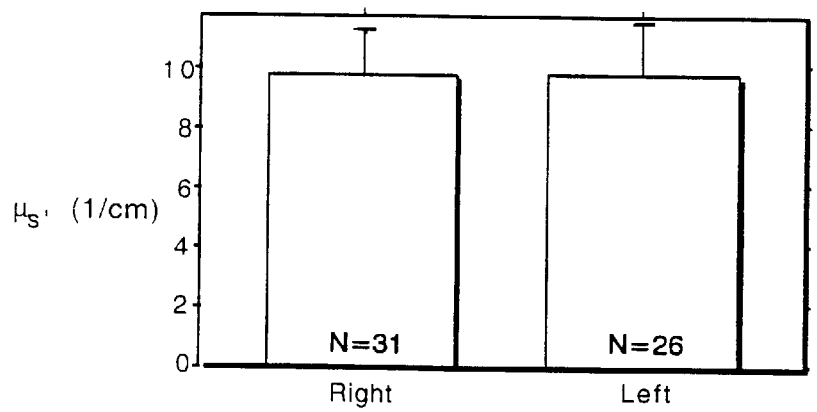
Figure 5D:
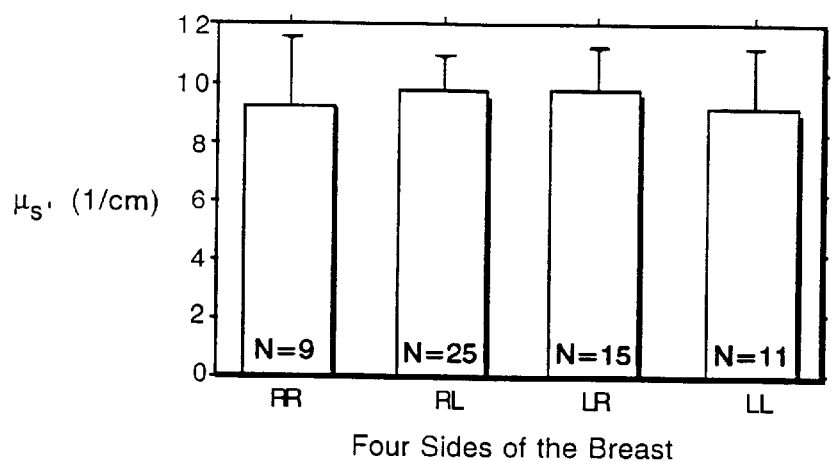
Figure 5F:
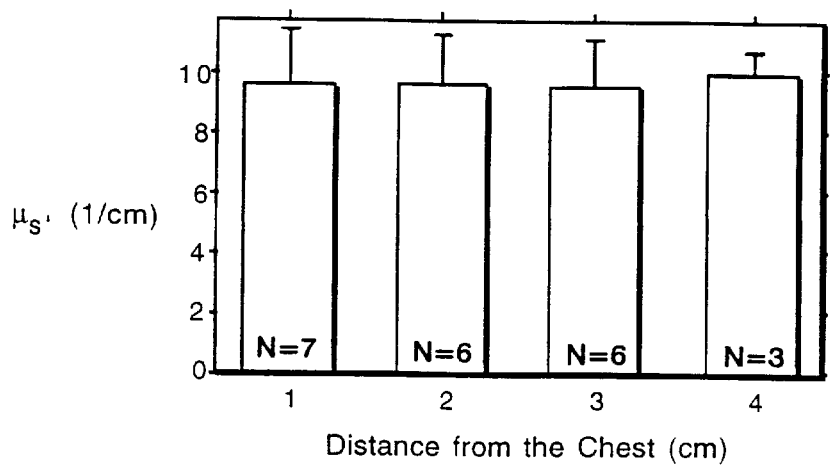

The examination of normal breast tissue was performed at several different locations of the right and left breast of the same woman. Referring to FIGS. 2 and 3, letters RR, LR, LR and LL denote the right and left breast and the right and left breast side where the input and detection ports were located, respectively. FIGS. 5A and 5B summarize the absorption coefficient ($\mu_a$) and the scattering coefficient ($\mu_s' = (1-g)\cdot\mu_s$), respectively, measured on the right and left breast at a separation $\rho$=6 cm. The values of $\mu_a$ and $\mu_s'$ for the right breast are identical to the values for the left breast within the measurement error. FIGS. 5C and 5D summarize $\mu_a$, $\mu_s'$, respectively, for the tissue on the left side and the right side of each breast, and FIGS. 5E and 5F summarize $\mu_a$, $\mu_s'$, respectively, for the tissue located at different distances from the chest wall. The data shown in FIGS. 5A through 5F confirm that there is no significant difference in the optical properties measured over the entire breast.

Figure 6A:
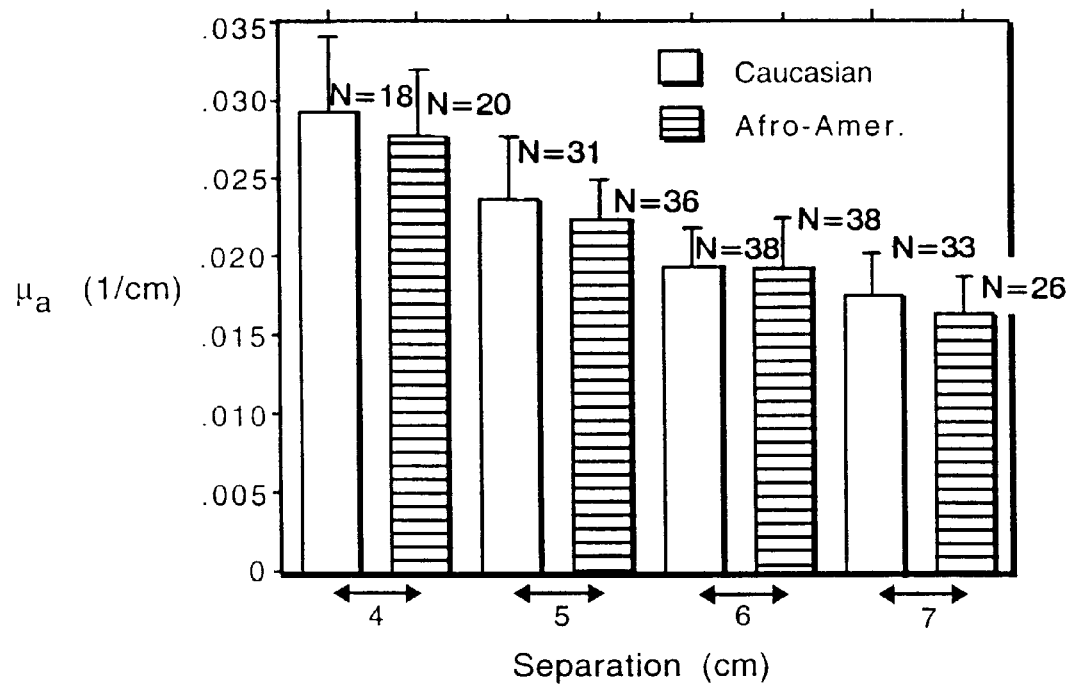
FIGS. 6A and 6B display values of the absorption coefficient and the scattering coefficient, respectively, of normal breast tissue for women of different ethnic background.
Figure 6B:
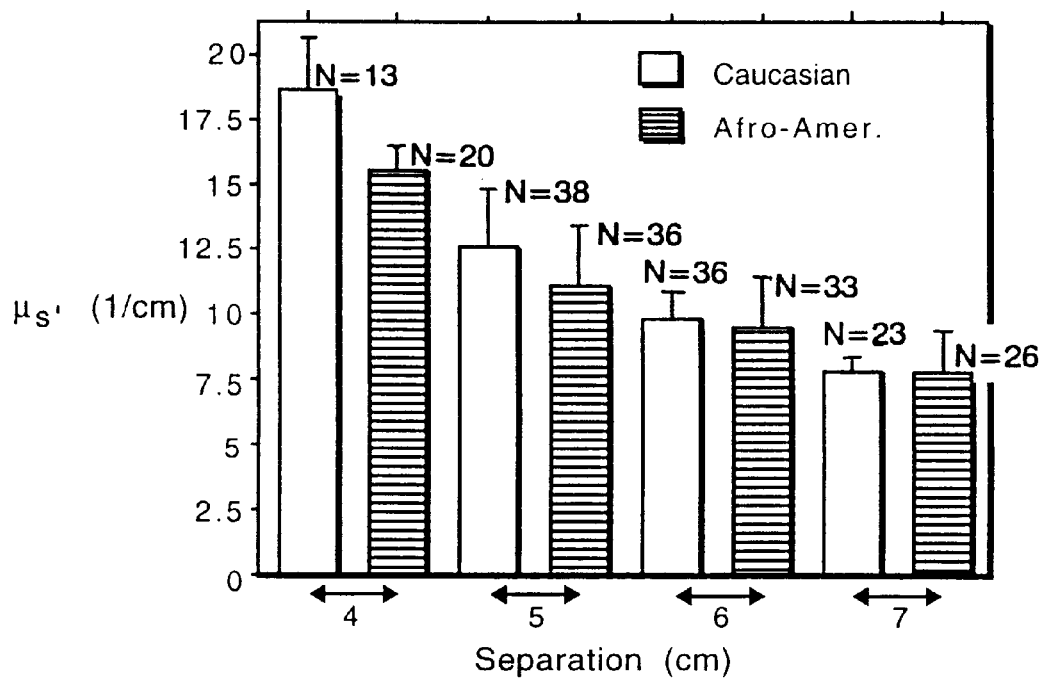

The examination of normal breast tissue also measured differences in the optical properties corresponding to the volume of the breast, type of the breast tissue, the age of the woman and ethnic background. Based on the decreasing X-ray background absorption, the breast tissue was categorized as "dense", "fatty", or a "mixture" of the two tissue types. The values of $\mu_a$ and $\mu_s'$ of "fatty" tissue are lower than for "dense" tissue, which has a higher fibrous content. Since the shape of the breast varies, it was difficult to categorize precisely the breast volume. For the volume measurement, the breast was stabilized on a plate and the length was measured from the chest to the end of the breast. The width and the thickness were measured at approximately 1 cm from the chest. Tissue of a large volume breast exhibits lower values of $\mu_a$ and $\mu_s'$ than that of a small volume breast. The same trend is observed for women above the age 50 when compared to women below 50. FIGS. 6A and 6B display values of $\mu_a$ and $\mu_s'$, respectively, for Caucasians and African-Americans. Normal breast tissue of Caucasians and African-Americans exhibits substantially the same optical properties except for the values of $\mu_s'$ measured at the 4 cm separation. Since the skin forms a higher relative percentage of the examined tissue at a smaller separation of the input and output ports, the lower values of $\mu_s'$ may be due to a lower scattering coefficient of the skin with more pigment.

In all measurements, a smaller separation of the input and output ports yielded larger values of $\mu_a$ and $\mu_s'$ than a larger separation of the ports. This differences can be explained by violation of the semi-infinite boundary conditions at the smaller separations, i.e., a larger escape of photons through the tissue surface before they are collected by optical fiber 17. Furthermore, this dependence exists since the slope of the photon decay was measured not sufficiently far from the peak of the reflectance data as expressed in Eqs. 1, 2 and 3.

This problem arises due to a low photon count of approximately 10,000 counts at the peak. Thus the measured data have a low signal to noise ratio and a reliable reflectance data can not be taken at $t \gg t_{max}$. The corresponding error in the absorption coefficient, $E(\rho,t)|_{abs}$, is determined using Eq. 7.

$$E(\rho, t)|_{abs} = \frac{1}{c}\left[-\frac{5}{2t} + \frac{\rho^2}{4DCT}\right] \quad (7)$$

The error of scattering coefficient, $E(\rho,t,\mu_a)|_{sct}$, arises due to the error in the absorption coefficient. The corresponding error is determined using Eq. 8.

$$E(\rho, t, \mu_a)|_{sct} = \frac{1}{3\rho^2}[4E(\rho, t)|_{abs} C^2 t_{max}^2] - E(\rho, t)|_{obs} \quad (8)$$

The preliminary values of $\mu_a$ and $\mu_s'$ corrected for the error using Eqs. 7. and 8 are shown in Table 1.

TABLE 1

| Separation (cm) | Mean $\mu_a$ | $\mu_a$ Mean Error Adjusted | Mean $\mu_s$ | Mean $t_{max}$ (ns) | $\mu_s$ Mean Error Adjusted |
|---|---|---|---|---|---|
| 4 | 0.029 | 0.020 | 16.2 | 1.55 | 14.1 |
| 5 | 0.023 | 0.021 | 11.4 | 1.9 | 10.9 |
| 6 | 0.019 | 0.022 | 9.5 | 2.3 | 10.1 |
| 7 | 0.017 | 0.021 | 7.9 | 2.7 | 8.7 |

The corrected values of mean $\mu_a$ for different separations, $\rho$, are substantially the same, but the corrected values of mean $\mu_s$ still are $\rho$ dependent although their spread is reduced considerably.

The examination of a breast with abnormal tissue was performed substantially the same way as the above-described examination of normal breast tissue. The breast tissue was first characterized by x-ray mammography and the size and location of a mass was determined. The examined breast was compressed between x-ray film case 90 and a support 12, as shown in FIG. 1C. Input port 14 and output port 16 were selected so that mass 7 was located in optical field 96.

The values of $\mu_a$ and $\mu_s'$ measured around tumor 7 (using input output port set 10b of FIG. 1A) were compared to control data measured on the same breast (using input output port sets 10a and 10c of FIG. 1A). The measured data were also correlated with pathology information on abnormalities in the examined breasts. The abnormalities were divided into the following three categories: fibrocystic, Fibroadenoma, and Carcinoma. Furthermore, these three categories are subdivided according to the size of the tumors as follows: smaller in diameter than 1 cm, and equal or larger in the diameter than 1 cm. Preliminary data measured on over fifty patients show an increase in the values of both $\mu_a$ and $\mu'$ when compared with normal tissue but statistical significance has not been demonstrated.

Other embodiments are within the following claims:

I claim:

1. A system for in vivo examination of biological tissue of a body part of a subject, comprising:

a light source constructed to generate pulses of light of a selected wavelength in the visible or infra-red range, said pulses having duration of less than about a nanosecond, a support, positionable relative to the examined body part, comprising an array of input and output ports separated by selected distances each said input port constructed to define an irradiation location on a surface of the body part, each said output port constructed to define a detection location on the surface of the body part, positions of said irradiation location and said detection location designating optical field of photon migration paths from said irradiation location to said detection location, said array being designed for systematic examination of a tissue volume of said body part by utilizing several of said optical fields, a detector, the light source and the detector optically connected respectively to at least one of the input and output ports, the detector constructed to detect over time photons of modified pulses of said selected wavelength that have migrated in the examined tissue between irradiation and detection locations and arrived at said detector, said detector constructed to produce corresponding electrical signals, a photon counter, connected to said detector, constructed to accumulate over time said electrical signals corresponding to a shape of said modified pulses, and a processor, connected to said photon counter, constructed and arranged to determine a physiological property of the examined tissue based on said accumulated electrical signals.

2. The system of claim 1 wherein said photon counter includes:

a gated integrator and an integrator timing control constructed to receive said electrical signals and integrate said signals over at least two selected time intervals separately spaced over arrival times of said modified pulses, and said processor further constructed and programmed to determine said physiological property by calculating a value of an absorption coefficient ($\mu_a$) using the number of said signals integrated over each time interval.

3. The system of claim 2 wherein said gated integrator, said integrator timing control, and said processor are further constructed to determine the delay time ($t_{max}$) between a time when a pulse is introduced and a time at which the corresponding modified pulse has the maximum value, and said processor being further constructed and programmed to determine the effective scattering coefficient $(1-g) \cdot \mu_s$ of the examined tissue.

4. The system of claim 1 wherein said photon counter includes:

a discriminator connected to a time-to-amplitude convertor constructed to receive said electrical signals and produce migration time signals corresponding to migration times of detected photons that have migrated in the tissue, and a multichannel analyzer constructed to receive and collect said migration time signals over arrival times of said modified pulses thereby determining said shape of the modified pulses; and said processor further constructed and programmed to determine said physiological property by calculating a value of an absorption coefficient ($\mu_a$) using said determined shape.

5. The system of claim 4 wherein said processor is further constructed and programmed to calculate the effective scattering coefficient $(1-g) \cdot \mu_s$ of the examined tissue using said determined shape.

6. The system of claim 1, 2, 3, 4 or 5 wherein said support is constructed for optical breast tissue examination, and said system further includes an X-ray film case constructed for cooperative optical breast tissue examination and X-ray mammography.

7. The system of claim 6 wherein said support further includes optical material of selected scattering and absorptive properties positionable on the skin of the examined breast.

8. The system of claim 1, 2, 3, 4 or 5 wherein said support is constructed for optical breast tissue examination and further includes an opening constructed for insertion of a needle for cooperative optical breast tissue examination and a needle localization procedure.

9. The system of claim 8 wherein said needle is constructed to insert a light guide into the breast tissue, one of said input ports being located at a distal end of said light guide.

10. The system of claim 8 wherein said support further includes optical material of selected scattering and absorptive properties positionable on the skin of the examined breast.

11. The system of claim 1, 2, 3, 4 or 5 wherein said support is constructed for optical breast tissue examination and further includes a network of magnetic coils, said support being constructed for cooperative optical breast tissue examination and MRI examination.

12. The system of claim 11 wherein said support further includes optical material of selected scattering and absorptive properties positionable on the skin of the examined breast.

13. A method for in vivo examination of biological tissue of a body part of a subject using pulses of light of a selected wavelength, said method comprising the steps of:

(a) providing a support, positionable relative to the examined body part, comprising an array of input and output ports separated by selected distances, each said input port being constructed to define an irradiation location on a surface of the body part, each said output port being constructed to define a detection location on the surface of the body part, positions of said irradiation location and said detection location designating optical field of photon migration paths from said irradiation location to said detection location, said array being designed for systematic examination of a tissue volume of said body part by utilizing several of said optical fields, (b) on a repeated basis, selecting a set of irradiation and detection locations and the corresponding input and output ports, (c) for each of said selections, introducing into the examined tissue, at the respective input port, pulses of light of a selected wavelength in the visible or infra-red range, said pulses having duration of less than a nanosecond, (d) for each of said selections detecting over time, at the respective output port, photons of modified pulses of said selected wavelength that have migrated in the examined tissue from said irradiation location to said detection location and arrived at said output port, (e) for each of said selections, accumulating, over arrival time of said detected photons, electrical signals corresponding to said detected photons of said modified pulses, (f) determining a physiological property of the examined tissue based on said accumulated electrical signals.

14. The method of claim 13 wherein said accumulating step includes integrating said electrical signals over at least two selected time intervals separately spaced over the arrival time of photons of said modified pulses, and said determining step including calculating a value of an absorption coefficient ($\mu_a$) of the examined tissue based on the number of photons integrated over each said time interval.

15. The method of claim 14 wherein said accumulating step further includes the step of integrating said photons over other selected time intervals separately spaced over the arrival time of said modified pulses, and the step of evaluating the time delay ($t_{max}$) between a time when a pulse is introduced and a time at which the corresponding modified pulse has the maximum value, based on the number of photons integrated over said time intervals, said determining step further includes calculating a value of a scattering coefficient ($\mu_s$) of the examined tissue by employing said absorption coefficient and said time delay.

16. The method of claim 13 wherein said accumulating step includes receiving said electrical signals and producing migration time signals corresponding to migration time of photons migrating in the tissue and collecting said migration time signals over arrival times of said modified pulses and determining a shape of said modified pulses; and said determining step including calculating a value of an absorption coefficient ($\mu_a$) of the examined tissue based on said determined shape.

17. The method of claim 16 wherein said accumulating step further includes calculating the effective scattering coefficient $(1-g) \cdot \mu_s$ of the examined tissue based on said determined shape.

18. The method of claim 13, 14, 15, 16 or 17 wherein said support is constructed for optical breast tissue examination in conjunction with x-ray mammography, and said method further includes performing x-ray mammography examination.

19. The method of claim 13, 14, 15, 16 or 17 wherein said support is constructed for optical breast tissue examination in conjunction with a needle localization procedure, and said method further includes performing the needle localization procedure.

20. The method of claim 19 wherein said needle localization procedure is performed with a needle that includes a light guide and one of said input ports, and said introducing step includes inserting said needle into a selected region of the breast to position said input port.

21. The method of claim 13, 14, 15, 16 or 17 wherein said support is constructed for optical breast tissue examination in conjunction with MRI examination, and said method further includes performing the needle localization procedure.

* * * * *